(12) United States Patent
McDonnell et al.

(10) Patent No.: US 8,236,492 B2
(45) Date of Patent: Aug. 7, 2012

(54) DECONTAMINATION OF PRION-CONTAMINATED SURFACES WITH PHENOLS

(75) Inventors: Gerald E. McDonnell, Basingstoke (GB); Herbert J. Kaiser, Pontoon Beach, IL (US); Kathleen M. Antloga, Chardon, OH (US); Shahin Kellor, St. Louis, MO (US)

(73) Assignee: Steris Inc., Mentor, OH (US)

( * ) Notice: Subject to any disclaimer, the term of this patent is extended or adjusted under 35 U.S.C. 154(b) by 112 days.

(21) Appl. No.: 12/711,446

(22) Filed: Feb. 24, 2010

(65) Prior Publication Data
US 2010/0248287 A1   Sep. 30, 2010

Related U.S. Application Data

(62) Division of application No. 10/637,149, filed on Aug. 8, 2003.

(51) Int. Cl.
*C12Q 1/70* (2006.01)
(52) U.S. Cl. .......................................... 435/5
(58) Field of Classification Search .................. None
See application file for complete search history.

(56) References Cited

U.S. PATENT DOCUMENTS

| | | | | |
|---|---|---|---|---|
| 5,185,371 | A | 2/1993 | Rubinstein | 422/28 |
| 6,720,355 | B2 * | 4/2004 | Prusiner et al. | 514/557 |
| 7,001,873 | B2 * | 2/2006 | McDonnell et al. | 510/161 |
| 7,252,720 | B2 * | 8/2007 | Foster et al. | 134/42 |
| 2003/0086820 | A1 | 5/2003 | McDonnell et al. | 422/28 |
| 2004/0106188 | A1 | 6/2004 | Kritzler et al. | 435/264 |

FOREIGN PATENT DOCUMENTS
GB   2 391 785   2/2004

OTHER PUBLICATIONS

Castle et al.; (1987) J. Gen. Virol., 68: 225-231.
Gasset et al.; (1993) PNAS 90: 1-5.
Prusiner; (1982) Sicence 216(9): 136-144.
Cai et al.; Biochimica et Biopohysica Acta. (2002) 1597: 28-35.
Nandi et al.; Biochemistry (2002) 41: 11017-11024.
Ernst & Race; "Comparative Analysis of Scrapie Agent Inactivation Methods"; Journal of Virological Methods; pp. 193-201; 1993.
Antloga et al.; "Prion Disease and Medical Devices"; ASAIO Journal; V. 46, N. 6, 2000; pp. S69-S72 XSP001092854.
Darbord; "Inactivation of Prions in Daily Medical Practice"; Biomedicine & Pharmacotheraphy, V. 54, 1999; pp. 34-38 XP002228686.
Rutala et al.; "Creutzfeld-Jakob Disease: Recommendations for Disinfection and Sterilization"; Clinical Infectious Diseases; V. 32, N. 9, May 2001; pp. 1348-1356 XP008012867.
Journal of Virological Methods; vol. 41, 1993, pp. 193-201 XP002316603; p. 196.
Polymenidou et al.; BMC Infectious Diseases; 2002; 2:23.
Race and Raymond; (2004) J. of Virol 78(4): 2164-2165.
Cooper; (1913) Biochem J 7(2)175-185.
Yamamoto et al.; (2001) J Vet Med Sci 63(9):983-990.
Werner et al.; Arch Environ Contam Toxicol (1983) 12:569-575.

* cited by examiner

*Primary Examiner* — Zachariah Lucas
*Assistant Examiner* — Michelle S Horning
(74) *Attorney, Agent, or Firm* — Renner, Otto, Boisselle & Sklar

(57) ABSTRACT

A method of decontaminating a surface or liquid which is contaminated with prions includes treating the surface with a composition which includes one or more phenol. Phenols which are particularly effective include p-chloro-m-xylanol, thymol, triclosan, 4-chloro, 3-methylphenol, pentachlorophenol, hexachlorophene, 2,2-methyl-bis(4-chlorophenol), and p-phenylphenol.

28 Claims, 4 Drawing Sheets

DECONTAMINATION OF PRION-CONTAMINATED SURFACES WITH PHENOLS

This application is a divisional of U.S. patent application Ser. No. 10/637,149 filed on Aug. 8, 2003, which is incorporated herein by reference in its entirety.

BACKGROUND OF THE INVENTION

The present invention relates to the field of biological decontamination. The invention finds particular application in connection with the removal and/or destruction of harmful biological materials, such as prions (proteinaceous-infectious agents), from medical, dental, and pharmaceutical instruments and will be described with particular reference thereto. It will be appreciated, however, that the method and system of the present invention may be utilized in biological decontamination of a wide range of equipment, instruments, and other surfaces contaminated with prion infected material, such as pharmaceutical preparation facilities, food processing facilities, laboratory animal research facilities including floors, work surfaces, equipment, cages, fermentation tanks, fluid lines, and the like.

The term "Prion" is used to describe proteinaceous-infectious agents that cause relatively similar brain diseases in humans and/or in animals, which are invariably fatal. These diseases are generally referred to as transmissible spongiform encephalopathies (TSEs). TSEs include Creutzfeldt-Jakob disease (CJD) and variant CJD (vCJD) in humans, Bovine Spongiform Encephalopathy (BSE) in cattle, also know as "Mad Cow Disease," Scrapie in sheep, and Wasting Disease in elk. All of these diseases attack the neurological organs of the animal or animals which are susceptible to the particular disease. They are characterized by initially long incubation times followed by a short period of neurological symptoms, including dementia and loss of coordination, and eventually death.

The infectious agent responsible for these diseases is thought to be a simple protein, with no associated nucleic acids. The pathogenic mechanism for such prion diseases is proposed to involve an initially normal host encoded protein. The protein undergoes a conformational change to an abnormal form (a prion), which has the ability of self-propagation. The exact cause of this change is, at present, unknown. The abnormal form of the protein is not broken down effectively in the body and its accumulation in certain tissues (in particular neural tissue) eventually causes tissue damage, such as cell death. Once significant neural tissue damage has occurred, the clinical signs are observed.

Prion diseases may thus be classified as protein aggregation diseases, which also include several other fatal diseases, such as Alzheimer's disease and amyloidosis. In the case of CJD, the most prevalent prion disease in humans (occurring in roughly 1:1,000,000 of the population), about 85% of cases are thought to arise sporadically, about 10% are thought to be inherited, and about 5% arise iatrogenically.

Although not considered to be highly contagious, prion diseases can be transmitted by certain high-risk tissues, including the brain, spinal cord, cerebral spinal fluids, and the eye. Iatrogenic transmission has been reported during several procedures, including dura-mater grafting, corneal transplants, pericardial homografts, and through human gonadotropin and human growth hormone contamination. Transmission via medical devices has also been reported, including from neurosurgical instruments, depth electrodes, and other devices used for surgical procedures in close proximity to the central nervous system. Concerns are being raised that procedures previously considered to be "low risk" in terms of prion infection, such as tonsillectomy and dental procedures, may pose unacceptable risks of infection, particularly, if the incidence of prion-related diseases increases.

After a surgical procedure on a prion infected patient, prion containing residue may remain on the surgical instruments, particularly neurosurgical and opthalmological instruments. During the long incubation period, it is extremely difficult to determine whether a surgical candidate is a prion carrier.

Different levels of microbial decontamination are recognized in the art. For example, sanitizing connotes free from dirt or germs by cleaning. Disinfecting calls for cleansing in order to destroy harmful microorganisms. Sterilization, the highest level of biological contamination control, connotes the destruction of all living microorganisms.

It is now known that certain biological materials, which do not live or reproduce in the conventional sense, such as prions, are nevertheless capable of replication and/or transformation into harmful entities. We use herein the term "deactivation" to encompass the destruction of such harmful biological materials, such as prions, and/or their ability to replicate or undergo conformational changes to harmful species.

Prions are notoriously very hardy and demonstrate resistance to routine methods of decontamination and sterilization. Unlike microorganisms, prions have no DNA or RNA to destroy or disrupt. Prions, due to their hydrophobic nature, tend to aggregate together in insoluble clumps. Under many conditions that lead to successful sterilization of microorganisms, prions form tighter clumps, which protect themselves and underlying prions from the sterilization process.

The World Health Organization (1997) protocol for prion deactivation calls for soaking the instrument in concentrated sodium hydroxide or hypochlorite for two hours followed by one hour in an autoclave. These aggressive treatments are often incompatible with medical devices, particularly flexible endoscopes and other devices with plastic, brass, or aluminum parts. Many devices are damaged by exposure to high temperatures. Chemical treatments, such as strong alkali, are damaging to medical device materials or surfaces in general. Glutaraldehyde, formaldehyde, ethylene oxide, liquid hydrogen peroxide, most phenolics, alcohols, and processes such as dry heat, boiling, freezing, UV, ionizing, and microwave radiation have generally been reported to be ineffective. There is a clear need for products and processes that are effective against prions yet compatible with surfaces.

Ernst and Race (J. Virol. Methods 41:193-202 (1993)) describe a study in which a phenol-based disinfectant product (LpH™, obtainable from STERIS Corp., Mentor, Ohio), which according to the authors, contains p-tertiary-amylphenol, o-benzyl-p-chlorophenol, and 2-phenyl phenol, was found to be effective against scrapie. The study investigated the effects of concentration (0.9-90%) and exposure time (0.5-16 hrs) on the level of infection removed in scrapie-sensitive hamster models injected with hamster brain homogenate. Relatively high concentrations of LpH™ or extended periods were found to be effective in reducing the presence of the prion. In other studies, phenols have generally been found not to be effective against prions.

The present invention provides a new and improved method of treatment of surfaces contaminated with prion-infected material, which overcomes the above-referenced problems and others.

SUMMARY OF THE INVENTION

In accordance with one aspect of the present invention, a method of treating a body which is contaminated with prions. The method includes contacting the body with a composition comprising a phenol to inactivate prions on the body.

In accordance with another aspect of the present invention, a method of determining the effectiveness of a phenol-based decontaminant composition on a material which is contaminated with prions is provided. The method includes combining a solution of the phenol-based decontaminant with a protein material, determining a measure of the phenol taken up by the material, and determining the effectiveness of the composition based on the amount of phenol taken up.

One advantage of the present invention is that it is gentle on instruments.

Another advantage of the present invention is that it deactivates prions quickly and effectively.

Another advantage of the present invention is that it is compatible with a wide variety of materials and devices.

Still further advantages of the present invention will become apparent to those of ordinary skill in the art upon reading and understanding the following detailed description of the preferred embodiments.

The following abbreviations are used throughout:

| | |
|---|---|
| BSA = | bovine serum albumin |
| OBPCP= | o-benzyl-p-chlorophenol |
| OPP = | o-phenylphenol |
| PCMX = | p-chloro, m-xylanol |
| PTAP = | p-tertiary-amylphenol |
| 3,4 DiOH benzoic = | 3,4 dihydroxybenzoic acid |
| 3,5 DiMeOphenol = | 3,5 dimethoxyphenol |
| 2,6 DiMeOphenol = | 2,6 dimethoxyphenol |
| 2,3 DiMe-phenol = | 2,3 dimethoxyphenol |

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
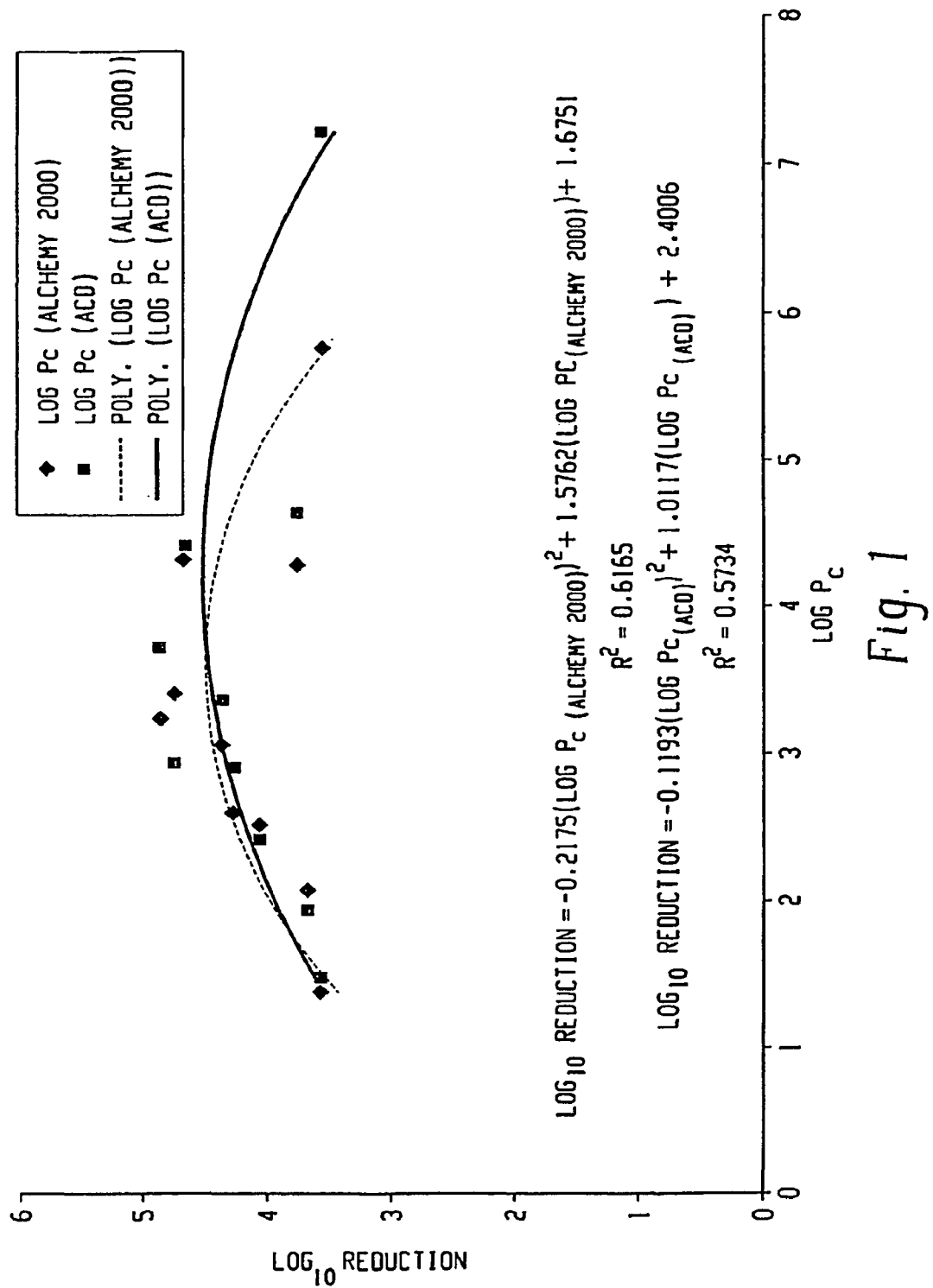
FIG. 1 is a plot showing Log reduction prions vs. the partition coefficient for various phenols.

A disinfectant composition, which is effective on a wide range of bodies, including surfaces and liquid bodies, for reduction or elimination of hazardous prions includes a phenol or combination of phenols. Surfaces for which the composition is effective at removing or substantially reducing the prion contamination include surfaces of instruments employed in medical, dental, and pharmaceutical procedures, surfaces of equipment used in the food and beverage processing industry and work surfaces, walls, floors, ceilings, fermentation tanks, fluid supply lines, and other potentially contaminated surfaces in hospitals, industrial facilities, research laboratories, and the like. Particular examples include the treatment of medical waste, such as blood, tissue and other body waste, prior to disposal, treatment of rooms, cages, and the like used for housing animals known or suspected to be infected with prions, decontamination of BSE infected areas, including slaughterhouses, food processing facilities, and the like, medical device reprocessing, decontamination of disinfection or sterilization systems, formulation of pharmaceuticals, medicaments, and cleaning agents having antifungal, antiviral, antituberculoidal, and antibacterial efficacy, as well as prion efficacy.

The composition includes one or more phenols. Suitable phenols include alkyl, chloro, and nitro-substituted phenols and biphenols, and carboxylic acids thereof. Exemplary phenols include, but are not limited to phenol; 2,3-dimethylphenol; 3,5-dimethoxyphenol (3,5 DiMeOphenol); 2,6-dimethoxyphenol (2,6 DiMeOphenol); o-phenylphenol (OPP); p-tertiary-amylphenol (PTAP); o-benzyl-p-chlorophenol (OBPCP); p-chloro, m-cresol (PCMC); o-cresol; p-cresol; 2,2-methylenebis(p-chlorophenol); 3,4-dihydroxybenzoic acid (3,4-DiOH benzoic); p-hydroxybenzoic acid; caffeic acid; protocatechuic acid; p-nitrophenol; 3-phenolphenol; 2,3-dimethoxyphenol (2,3 DiMe-phenol); thymol; 4 chloro, 3-methoxyphenol; pentachlorophenol; hexachlorophene; p chloro-m-xylanol (PCMX); triclosan; 2,2-methoxy-bis(4-chloro-phenol); and para-phenylphenol.

It has been found that phenols with a relatively high hydrophobicity tend to be more effective in the composition. $P_c$ is defined as the calculated octanol-water partition coefficient. Higher Log $P_c$ values indicate the substance is more hydrophobic. Software available for determining $P_c$ values is available for example from Advanced Chemistry Development Software. Preferably at least one of the phenols in the composition has a Log $P_c$ value of at least 2.5, more preferably, at least about 3, and up to about 6.0, as measured by the ACD software method. It has been found that the higher the Log P value (more hydrophobic) the more phenol is absorbed. Accordingly, lower phenol concentrations can be used when the phenol is hydrophobic to achieve the desired prion destruction. One particularly preferred phenol having a Log $P_c$ value of 3.35 is PCMX.

The composition is preferably acidic, i.e., has a pH of neutral (pH 7), or below, more preferably, a pH of about 6, or above, most preferably, a pH of about 2.5. For example, the composition may include an organic or inorganic acid which is added to adjust the pH, such as hydrochloric acid, glycolic acid, phosphoric acid, or the like. It is also contemplated that the composition may be alkaline, for example, a base is added to adjust the pH, such as sodium hydroxide, potassium hydroxide, or the like. Preferably the alkalinity is such that no more than 50% of the phenol is ionized.

The composition includes water or other suitable solvent. The composition is preferably provided as a concentrate, which is diluted in water to form a decontaminant solution of a suitable concentration for decontamination. Preferably, the concentrate is diluted to about a 1% by weight of the solution. For more rigorous decontamination, the concentrate can be used at higher concentrations, e.g., at about 5% by weight of the solution, or more. Unless otherwise specified, all concentrations are provided for the concentrate.

Preferably, the total molar phenol concentration of the concentrate is about 0.1M-1.0M, or greater, more preferably, about 0.2M, or greater, and most preferably, about 0.5M, or greater. Effective compositions which destroy at least 99% of harmful proteins (e.g., prions) have been formulated with total phenol concentrations of about 0.2M-0.5M, or greater.

The composition may also include other ingredients, depending on the specific application. Suitable ingredients include sequestering agents for removing water hardness salts, cosolvents, surfactants, corrosion inhibitors, buffering agents, and the like.

The sequestering agent is preferably an organic acid, inorganic acid, or a mixture thereof. Suitable organic acids include mono- and di-aliphatic carboxylic acids, hydroxy-containing organic acids, and mixtures thereof. Exemplary sequestering agents include glycolic acid, salicylic acid, succinic acid, lactic acid, tartaric acid, sorbic acid, sulfamic acid, acetic acid, benzoic acid, capric acid, caproic acid, cyanuric acid, dihydroacetic acid, dimethylsulfamic acid, propionic acid, polyacrylic acid, 2-ethyl-hexanoic acid, formic acid, fumaric acid, 1-glutamic acid, isopropyl sulfamic acid, naphthenic acid, oxalic acid, valeric acid, benzene sulfonic acid, xylene sulfonic acid, citric acid, cresylic acid, dodecylbenzene sulfonic acid, phosphoric acid, boric acid, phosphoric acid, and combinations thereof, with glycolic acid being preferred. For alkaline compositions, the acid sequestering agent may be omitted.

The acid is preferably present at a concentration of about 2-25% of the concentrate composition, more preferably, about 5-20%, more preferably, about 15-20%.

Suitable cosolvents include polyols containing only carbon, hydrogen and oxygen atoms. Exemplary polyols are $C_2$ to $C_6$ polyols, such as 1,2-propanediol, 1,2-butanediol, hexylene glycol, glycerol, sorbitol, mannitol, and glucose. Higher glycols, polyglycols, polyoxides and glycol ethers are also contemplated as co-solvents. Examples of these include alkyl ether alcohols such as methoxyethanol, methoxyethanol acetate, butyoxyethanol (butyl cellosolve), propylene glycol, polyethylene glycol, polypropylene glycol, diethylene glycol monoethyl ether, diethylene glycol monopropyl ether, diethylene glycol monobutyl ether, tripropylene glycol methyl ether, propylene glycol methyl ether, dipropylene glycol methyl ether, propylene glycol methyl ether acetate, dipropylene glycol methyl ether acetate, ethylene glycol n-butyl ether, 1,2-dimethoxyethane, 2-ethoxy ethanol, 2-ethoxyethylacetate, phenoxy ethanol, and ethylene glycol n-propyl ether. Combinations of co-solvents may be used. The polyol is preferably present as a concentration of at least 10%, more preferably, at least 20% and can be up to 40%.

Suitable surfactants include, anionic, cationic, non-ionic, zwitterionic surfactants. Anionic surfactants, such as alkylaryl anionic surfactants are particularly preferred. Exemplary surfactants include dodecylbenzene sulfonic acid and sodium 1-octane sulfonate, and combinations thereof.

Also useful anionic surfactants are sulfates, sulfonates, particularly $C_{14}$-$C_{18}$ sulfonates, sulfonic acids, ethoxylates, sarcosinates, and sulfosuccinates such as sodium lauryl ether sulfate, triethanolamine lauryl sulfate, magnesium lauryl sulfate, sulfosuccinate esters, ammonium lauryl sulfate, alkyl sulfonates, sodium lauryl sulfate, sodium alpha olefin sulfonates, alkyl sulfates, sulfated alcohol ethoxylates, sulfated alkyl phenol ethoxylates, sodium xylene sulfonate, alkylbenzene sulfonates, triethanolamine dodecylbenzene sulfonate, sodium dodecylbenzene sulfonate, calcium dodecylbenzene sulfonate, xylene sulfonic acid, dodecylbenzene sulfonic acid, N-alkoyl sarcosinates, sodium lauroyl sarcosinate, dialkylsulfosuccinates, N-alkoyl sarcosines, lauroyl sarcosine, and combinations thereof.

The composition may also include one or more soluble inorganic salts, such as sodium chloride. Sodium chloride has been found to increase the effectiveness of certain phenols, particularly those which are not halogenated, such as OPP, while the effect on halogenated phenols, such as PCMX, is less marked.

An exemplary concentrate composition is as follows:

| Ingredient | % by Weight of Composition |
|---|---|
| Water | Q.S., typically, about 35.0% |
| Sequestering agent, e.g., | |
| Glycolic acid | 0-25%, preferably, about 18.0 |
| Surfactants, e.g., | |
| Dodecylbenzene Sulphonic acid | 2-10%, preferably, about 7.0% |
| Sodium $C_{14}$-$C_{16}$ Sulfonate | 3-10%, preferably, about 6.0% |
| Cosolvent, e.g., | |
| Hexylene Glycol | 10-40%, preferably about 24.0% |
| Phenols, e.g., | |
| OBPCOP | 2-15%, preferably, about 9.0% |
| OBPCOP | 0.2-5%, preferably about 1.0% |

In one embodiment, at least some of the OBPCOP or OBPCOP is replaced with a phenol which is more effective than either of these phenols, such as PCMX.

Such a composition has been shown to be effective against prion-contaminated surfaces when diluted to a concentration of 1% by weight of the concentrate in water. While the mechanism of inactivating prions is not fully understood, it is contemplated that the phenol may form a complex with the prion protein, rendering it harmless. The prion is then unable to replicate to produce further prions. Studies by the inventors suggest that the phenol generally does not break down the prion. It is proposed that a change in the three dimensional structure of the prion protein results from interactions with the phenol, inactivating the prion.

Further, the composition is compatible with a wide range of surfaces, as compared with conventional prion treatments, such as high temperatures or high concentrations of sodium hypochlorite or sodium hydroxide.

The composition may be applied in a variety of ways, including by spraying, coating, immersion, or the like. In one embodiment, the composition is applied in the form of a gel. In this embodiment, a thickening agent, such as a natural or modified cellulose, is added to the formulation to increase the viscosity.

Other synthetic polymers, including polyacetates, natural gems, inorganic polymers such as synthetic clays, surfactants such as block copolymers and cationic surfactants may be used as a thickener.

The composition may be applied at room temperature, although higher temperatures are preferred. It has been found that by heating the composition to at least 30° C., more preferably, around 40° C., or above, a substantial shortening in the time required for inactivation of prions is achieved.

The effectiveness of various formulations of the composition may be investigated using human or other animal prion. Alternatively, a prion model, e.g., a protein such as bovine serum albumin (BSA) may be used to evaluate formulations. A preferred prion model is an ileal fluid dependant organism (IFDO). IFDO's were identified by Burdon, et al. (Burdon, *J. Med. Micro.*, 29: 145-157 (1989)) and described as being similar to prions in many respects, e.g., in resistance to disinfection and sterilization methods. Due to the ability to culture IFDO's artificially and detect them in the laboratory they provide a good model system for studying the effect of decontamination processes on prion inactivation. In an exemplary embodiment, the IFDOs are artificially cultured in a modified Mycoplasma base broth (Oxoid) and quantified by serial dilutions and plating on a similar agar. The efficacy of the decontamination formulations is preferably studied by suspension testing at room temperature at about a 1% dilution of the concentrate composition in water, simulating use of the composition. Following suitable contact times, aliquots are sampled and quantified by serial dilution and plating into modified Mycoplasma agar. The plates are preferably incubated at about 37° C. for several hours, preferably about 48 hours. The plates are examined and the number of colonies visible are counted. Log reductions may then be determined (log reduction is a measure of the number of organisms removed expressed as the difference between the $Log_{10}$, of the initial number of organisms minus the $Log_{10}$, of the number of organisms after treatment. E.g., a 6 log reduction means that out of one million initial organisms a maximum of one remains after treatment).

Breakdown studies with bovine serum albumin (BSA) using SDS-PAGE techniques show that the BSA is not broken down to any significant extent by the disinfectant LpH™. It has been proposed, therefore, that LpH™ and other phenol-based compositions have a subtle effect on the secondary or tertiary structure of the protein, rendering it no longer harmful.

It has been found that the solubility of the phenol in the composition has an effect on the degree to which the protein is complexed. In general, the lower the solubility of the phenol in the formulation, the greater the degree of complexation—i.e., the more effective the phenol formulation is at prion inactivation. Solubility is affected by the choice of phenol and the type and concentrations of other ingredients in the formulation, e.g., the solvents and cosolvents used.

Without intending to limit the scope of the present invention, the following Examples show the effects of various disinfectant compositions on a simulated prion model.

EXAMPLES

Example 1

Study of the Effect of Phenol Concentration on the Effectiveness of the Composition To test the contribution of various formulation effects on the priocidal activity of various compositions experiments are performed using IFDO log reduction as the response. The ingredients of compositions I-VII are listed in Table 1. Composition I is a commercial formulation, LpH™.

The IFDOs are artificially cultured in a modified Mycoplasma broth and quantified by serial dilutions and plating on a similar agar. The efficacy of the compositions I-VII is studied by suspension testing at room temperature at a 1% dilution of the composition in water. Following a suitable contact time, e.g., 10 minutes, aliquots are sampled and quantified by serial dilution and plating into modified Mycoplasma agar. Following incubation at 37° C. for 48 hours, the plates are evaluated by counting visible colonies and log reductions are determined. Results with the compositions are compared with an existing phenolic product are shown in Table 1.

TABLE 1

| Ingredient | % By Weight of Component in Concentrate | | | | | | | |
| --- | --- | --- | --- | --- | --- | --- | --- | --- |
| | I | II | III | IV | V | VI | VII | VIII |
| Water | 35.00 | 41.90 | 41.00 | 47.00 | 34.90 | 40.00 | 35.90 | 37.95 |
| Glycolic Acid | 18.00 | 18.00 | 18.00 | 18.00 | 18.00 | 18.00 | 18.00 | 18.00 |
| Dodecyl-benzene Sulfonic acid | 7.00 | 7.00 | 7.00 | 7.00 | 14.00 | 14.00 | 7.00 | 10.50 |
| Sodium C14-C16 Sulfonate | 6.00 | 12.00 | 12.00 | 6.00 | 12.00 | 6.00 | 6.00 | 9.00 |
| Hexylene glycol | 24.00 | 12.00 | 12.00 | 12.00 | 12.00 | 12.00 | 24.00 | 18.00 |
| o-Benzyl-p-Chlorophenol | 9.00 | 9.00 | 9.00 | 9.00 | 9.00 | 9.00 | 9.00 | 6.00 |
| o-Phenylphenol | 1.00 | 0.10 | 1.00 | 1.00 | 0.10 | 1.00 | 0.10 | 0.55 |
| Log Reduction | 5.1 | 4.8 | 4.9 | 5.2 | 5.7 | 4.8 | 6.7 | 5.2 |

*Initial count: $log_{10}$ 6.7 per mL.

A comparative study with LpH™ gave a Log reduction of 4.0 IFDO after treatment. Based on the Log Reductions obtained, Example VII was the best, since a 6.7 Log Reduction was obtained (i.e., no visible colonies).

Example 2

Effect of Approximately Equimolar Concentrations of Phenols

Various phenols at approximately equimolar concentrations (where possible when solubility permitted) are studied by the method of EXAMPLE 1. TABLE 2 shows the ingredients by weight for formulations IX-XX and the results obtained.

TABLE 2

| Ingredient | Molecular wt | Mol Phenol/ 100 g | IX | X | XI | XII | XIII | XIV |
| --- | --- | --- | --- | --- | --- | --- | --- | --- |
| 2,3-Dimethylphenol | 122.17 | 0.090 | 11.00 | | | | | |
| o-Benzyl-p-Chlorophenol | 218.69 | 0.086 | | 18.86 | | | | |
| o-Phenylphenol | 142.58 | 0.084 | | | 14.29 | | | |
| p-Chloro-m-Cresol | 156.61 | 0.087 | | | | 12.45 | | |
| p-Chloro-m-Xylenol | 150.2 | 0.099 | | | | | 15.50 | |
| 2,4,5-Trichlorophenol | 197.46 | 0.090 | | | | | | 17.80 |
| Hexylene Glycol | | | 4.00 | 3.95 | 6.29 | 4.21 | 4.00 | 4.23 |
| iso-Propyl alcohol | | | 8.00 | 7.90 | 7.62 | 8.14 | 8.40 | 8.08 |
| Sodium | | | 22.46 | 18.86 | 20.60 | 19.92 | 19.80 | 19.60 |

TABLE 2-continued

| Ingredient | | | | | | | |
|---|---|---|---|---|---|---|---|
| Laurylsulfate | | | | | | | |
| Alpha olefin sulfonate | | 6.70 | 6.32 | 6.10 | 6.03 | 7.00 | 6.45 |
| Glycolic Acid | | 19.00 | 18.68 | 17.14 | 18.30 | 21.00 | 18.00 |
| Triethanolamine | | 2.50 | 1.43 | 0.95 | 1.34 | 1.40 | 1.02 |
| Soft Water | | 26.34 | 24.00 | 27.01 | 29.61 | 22.90 | 24.82 |
| Log Reduction | | 4.1 | 4.7 | 4.8 | 4.3 | 4.4 | 4.9 |

| Ingredient | Molecular wt | Mol Phenol/ 100 g | XV | XVI | XVII | XVIII | XIX | XX |
|---|---|---|---|---|---|---|---|---|
| 2,2-Methylenebis (4-chlorophenol) | 122 | 0.051 | 6.17 | | | | | |
| Hexachlorophene | 406.9 | 0.026 | | 10.56 | | | | |
| p-Cresol | 108.1 | 0.086 | | | 9.33 | | | |
| Phenol | 94.1 | 0.090 | | | | 8.46 | | |
| Thymol | 150.2 | 0.090 | | | | | 13.52 | |
| Triclosan | 289.4 | 0.056 | | | | | | 16.18 |
| Hexylene Glycol | | | 3.81 | 15.96 | 4.17 | 4.10 | 4.01 | 10.95 |
| isopropyl alcohol | | | 14.42 | 20.57 | 7.96 | 8.26 | 8.00 | 20.79 |
| Sodium Laurylsulfate | | | 19.41 | 17.76 | 19.02 | 19.91 | 19.11 | 16.93 |
| Alpha Olefin Sulfonate | | | 7.26 | 12.70 | 6.26 | 6.28 | 6.29 | 3.98 |
| Glycolic Acid | | | 22.14 | 18.38 | 18.00 | 17.92 | 18.00 | 11.81 |
| Triethanolamine | | | 1.48 | 1.45 | 1.00 | 1.00 | 1.00 | 0.68 |
| Soft Water | | | 25.31 | 2.62 | 34.26 | 34.07 | 30.07 | 18.68 |
| Log Reduction | | | 3.8 | 3.6 | 3.7 | 3.6 | 3.2 | 2.7 |

Based on the Log values obtained, Formulation XIV with 2,4,5-Trichlorophenol achieved the greatest Log Reduction (4.9) better than the Log Reduction (4.0) achieved with LpH.

Example 3

Correlation of Results with Partition Coefficients ($P_c$)

$P_c$ is defined as the calculated octanol-water partition coefficient. The log $P_c$ values are calculated using two methods. The first method uses Alchemy 2000 Molecular Modeling Software (Tripos) along with a data set developed by STERIS Corporation. The second method uses Advanced Chemistry Development (ACD) Software Solaris v4.67 (© 1994-2002 ACD). The calculated log $P_c$ values for each phenol are shown in TABLE 3: These values are compared with Log reduction colonies obtained in Example 2.

TABLE 3

| Phenol | Log $P_c$ (Alchemy 2000) | Log $P_c$ (ACD) | $Log_{10}$ Reduction of Colonies |
|---|---|---|---|
| Phenol | 1.39 | 1.48 | 3.6 |
| p-Cresol | 2.08 | 1.94 | 3.7 |
| 2,3-Dimethylphenol | 2.50 | 2.40 | 4.1 |
| p-Chloro-m-cresol | 2.58 | 2.89 | 4.3 |
| p-Chloro-m-xylenol | 3.05 | 3.35 | 4.4 |
| 2,4,5-Trichlorophenol | 3.23 | 3.71 | 4.9 |
| Thymol | 3.27 | 3.28 | 3.2 |
| o-Phenylphenol | 3.40 | 2.94 | 4.8 |
| 2,2-Methylenebis(4-chlorophenol) | 4.27 | 4.62 | 3.8 |
| o-Benzyl-p-chlorophenol | 4.32 | 4.41 | 4.7 |
| Triclosan | 4.51 | 5.82 | 2.7 |
| Hexachlorophene | 5.75 | 7.20 | 3.6 |

Figure 2:
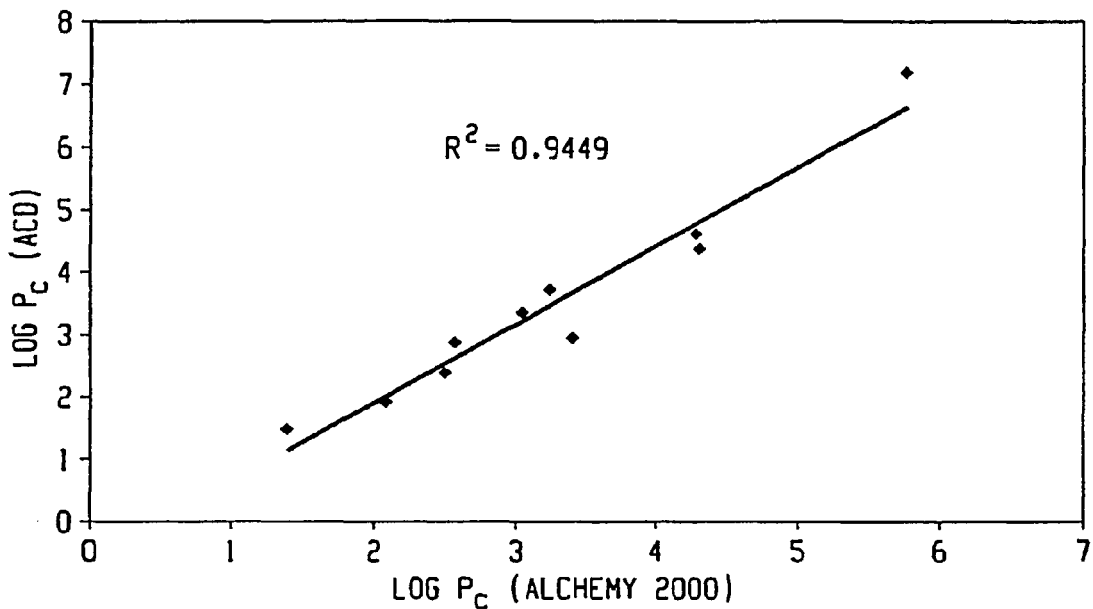
FIG. 2 is a plot showing the correlation between partition coefficients obtained by different methods.

FIG. 1 shows the Log IFDO reduction vs Log $P_c$ (Alchemy 2000) and the Log $P_c$ (ACD) values. The correlation between the Log $P_c$ (Alchemy 2000) and the Log $P_c$ (ACD) values is shown in FIG. 2.

Except for Triclosan and thymol, the activity of the phenols appear to correlate with the log $P_c$ associated with the phenol. Thymol and Triclosan were not included in this graph and the subsequent graph due to their apparent lack of fit. The two methods for calculating log $P_c$ agree fairly well with each other.

In general, phenols having a log $P_c$ value between 2 and 6.5, as measured by either of the above methods, display enhanced activity.

The phenols in the LpH™ product were found to be the most significant requirement for efficacy and were rated as OBPCP>>OPP>PTAP. When tested with equivocal concentrations of these phenols, the optimal combinations were shown to be formulation containing either OPBCP or OPP; PTAP was less effective.

The effect of phenols against prions does not appear to involve breakdown of the protein. This was shown in protein breakdown studies with BSA by SDS-PAGE. On exposure to the phenol formulations the protein appeared intact. It may be concluded that phenols have an unexpected subtle effect on the secondary or tertiary structure of the prion protein or in some way renders them non-infectious.

Example 4

Effect of Temperature on Phenol Formulation Activity

The IFDO's are artificially cultured in a modified Mycoplasma broth and quantified by serial dilutions and plating on a similar agar. The effect of temperature on phenol formulation activity is studied by suspension testing at a 1% dilution of the composition in water at various temperatures (20 and 40° C.). Following 5, 10, 15 and 20 minute contact times, aliquots are sampled and quantified by serial dilution and plating into modified Mycoplasma agar. After incubation at 37° C. for 48 hours, the plates are evaluated by counting visible colonies and log reductions are determined. Results comparing the phenol composition (LpH) at 20 and 40° C. are shown in FIG. 3.

Figure 3:
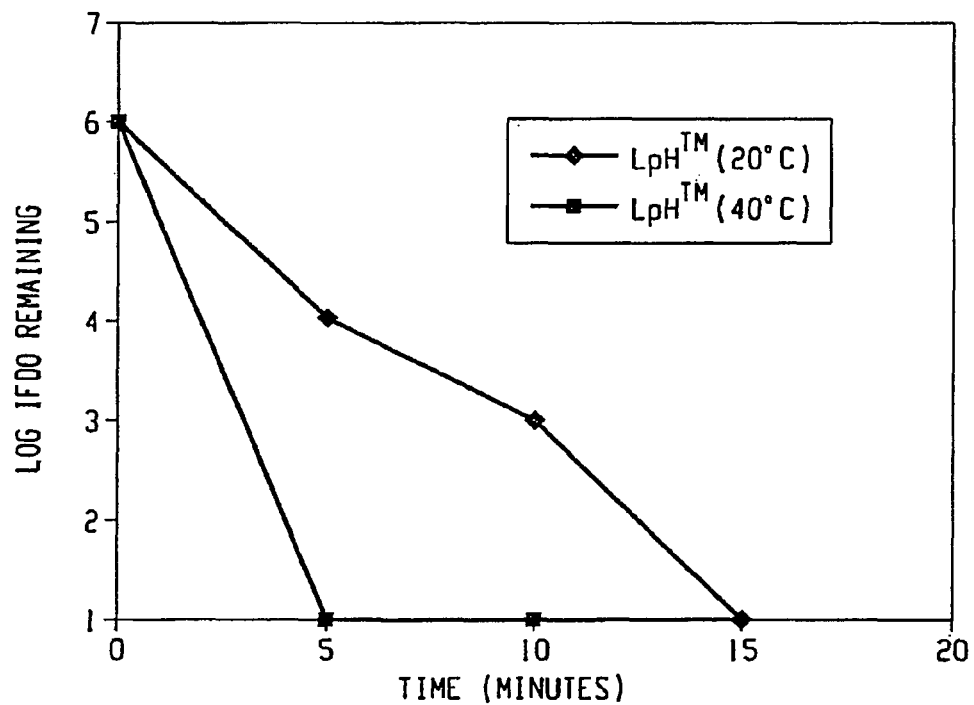
FIG. 3 is a plot showing the effect of temperature on the reduction of prions by phenols.

As shown in FIG. 3, IFDO levels were reduced to below detectable levels (i.e., greater than 1 Log) in 5 minutes at 40° C., as compared to 15 minutes at 20° C.

Example 5

Interactions of Phenol Formulations with BSA Protein

Figure 4:
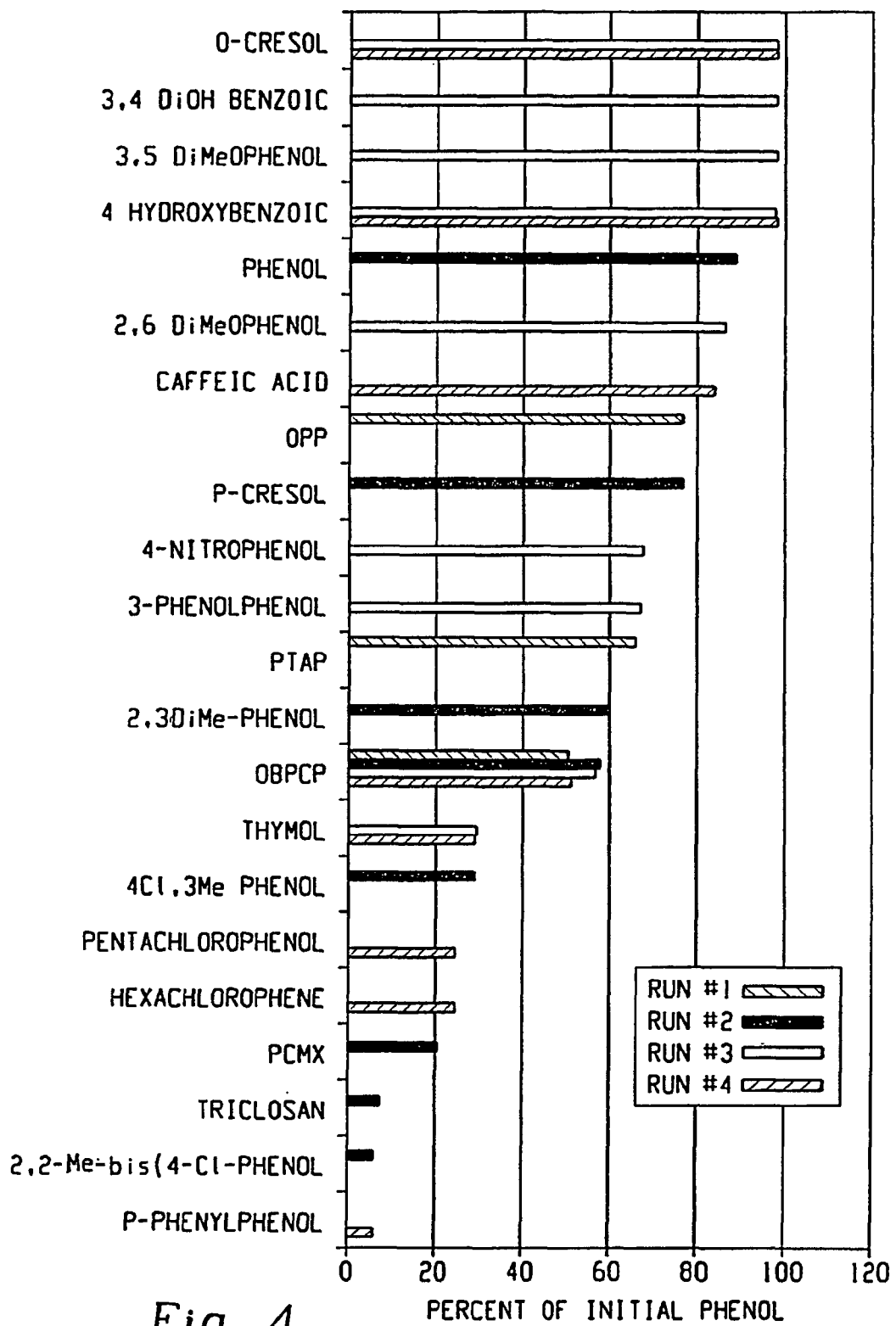
FIG. 4 is a plot showing the interactions of various phenols with BSA.

Phenol solutions with different phenols were prepared as follows: about 1.38 grams of a mixture of a phenol with solubilizers, such as anionic surfactants, an organic acid, isopropyl alcohol, glycols, and an amine was dissolved in 99 mL of water to form a solution containing a total phenol concentration of 4 mM. About 1 g of BSA was added to the phenol solution to give a concentration of about 0.15 mM BSA (the molecular weight of BSA is presumed to be about 66,000 Daltons). The solution was stirred for 15 minutes and then centrifuged at 1800 rpm for five minutes. Aliquots were analyzed by high performance liquid chromatography (HPLC). FIG. 4 shows the results for 4 runs in terms of the percent of the initial phenol present which was absorbed by the BSA. The percent absorbed showed good correlation with the amount of precipitate which formed. Based on these results, the absorption is a good way of determining a phenol's effectiveness against prions.

Example 6

Figure 5:
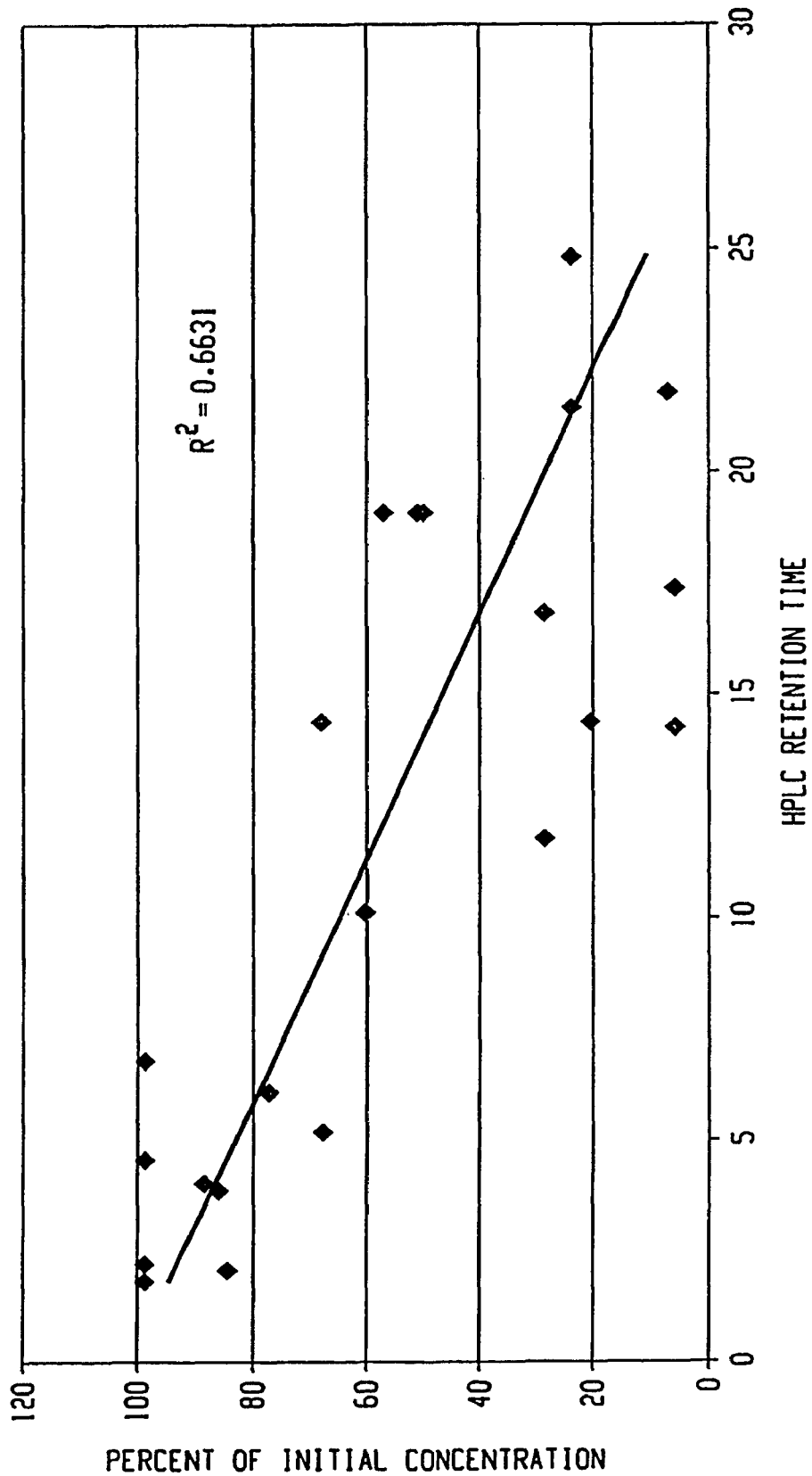
FIG. 5 is a plot of the percentage of initial concentration absorbed vs the HPLC retention time of various phenols.

The percentages of initial concentration absorbed from Example 5 were plotted against the HPLC retention time of the phenol. FIG. 5 shows the correlation between these values. A correlation coefficient of 0.81 was obtained, suggesting that HPLC retention time is a fairly good predictor of the absorption of phenol by the protein.

Example 7

Log $P_c$ (computer calculated) values for several phenols were plotted against equivalents absorbed. The results show that the higher the Log P value (more hydrophobic) the more phenol is absorbed. Accordingly, lower phenol concentrations can be used when the phenol is hydrophobic to achieve the desired prion destruction.

Example 8

100 mL of water with varying amounts of brine and phenol were studied for phenol uptake. The results are shown in Table 4. The excipient included a mixture of surfactants.

The results show that the presence of brine in the solution had a significant impact on phenol uptake when present at 2.5% or 5% by weight.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A method of determining the effectiveness of a phenol-based decontaminant composition on a material which is contaminated with prions comprising:
   combining a solution of the phenol-based decontaminant with a protein material;
   measuring the amount of phenol taken up by the protein material; and,
   determining the effectiveness of the composition based on the amount of phenol taken up.

2. The method of claim 1, wherein the protein material includes at least one of a prion-containing material and bovine serum albumin.

3. The method of claim 1 wherein the phenol-based decontaminant composition comprises one or more phenols.

4. The method of claim 3 wherein the one or more phenols comprise an alkyl, chloro, or nitro-substituted phenol or biphenol, or a carboxylic acid thereof.

5. The method of claim 3 wherein the one or more phenols comprise phenol; o-benzyl-p-chlorophenol; o-phenylphenol; 2,3-dimethylphenol; 3,5-dimethoxyphenol; 2,6-dimethoxyphenol; p-tertiary-amylphenol; p-chloro-m-cresol; o-cresol; p-cresol; 2,2-methylenbis(p-chlorophenol); 3,4-dihydroxybenzoic acid; p-hydroxybenzoic acid; caffeic acid; protocatechuic acid; p-nitrophenol; 3-phenol phenol; 2,3-dimethoxyphenol; thymol; 4-chloro-3-methoxyphenol; pentachlorophenol; hexachlorophene; p-chloro-m-xylenol; triclosan; 2,2-methoxy-bis(4-chloro-phenol); p-phenylphenol, or a mixture of two or more thereof.

6. The method of claim 1 wherein the phenol-based decontaminant composition comprises a surfactant.

7. The method of claim 6 wherein the surfactant comprises an anionic, cationic, non-ionic, or zwitterionic surfactant.

8. The method of claim 6 wherein the surfactant comprises an alkylaryl anionic surfactant.

9. The method of claim 6 wherein the surfactant comprises a $C_{14}$-$C_{18}$ sulfonate, a sulfonic acid, an ethoxylate, a sarcosinate, a sulfosuccinate, or a mixture of two or more thereof.

TABLE 4

| Run | Temp | Brine | Phenol | Excipient (% by wt) | BSA Ratio | Phenol-Conc (% by wt) | Phenol Uptake | % of initial |
|---|---|---|---|---|---|---|---|---|
| 1 | 35 | 0 | OPP | 1 | 30 | 0.8 | 1.47 | 95.2 |
| 2 | 27.5 | 2.5 | OPP | 1.25 | 26 | 2.4 | 18.42 | 30.4 |
| 3 | 20 | 5 | OPP | 1 | 22 | 4 | 16.66 | 25.5 |
| 4 | 35 | 5 | PCMX | 1.5 | 22 | 0.8 | 15.38 | 29.1 |
| 5 | 20 | 0 | PCMX | 1.5 | 30 | 4 | 26.74 | 11.2 |
| 6 | 27.5 | 2.5 | PCMX | 1.25 | 26 | 2.4 | 21.43 | 17.8 |
| 7 | 35 | 0 | PCMX | 1 | 22 | 4 | 15.34 | 30.2 |
| 8 | 27.5 | 2.5 | PCMX | 1.25 | 26 | 2.4 | 20.3 | 21.7 |
| 9 | 27.5 | 2.5 | OPP | 1.25 | 26 | 2.4 | 18.16 | 30.8 |
| 10 | 20 | 0 | OPP | 1.5 | 22 | 0.8 | 7.58 | 66.3 |
| 11 | 20 | 5 | PCMX | 1 | 30 | 0.8 | 21.46 | 30.4 |
| 12 | 35 | 5 | OPP | 1.5 | 30 | 4 | 25.48 | 15.4 |

10. The method of claim 6 wherein the surfactant comprises sodium lauryl ether sulfate, triethanolamine lauryl sulfate, magnesium lauryl sulfate, a sulfosuccinate ester, ammonium lauryl sulfate, an alkyl sulfonate, sodium lauryl sulfate, a sodium alpha olefin sulfonate, an alkyl sulfate, a sulfated alcohol ethoxylate, a sulfated alkyl phenol ethoxylate, sodium xylene sulfonate, an alkylbenzene sulfonate, triethanolamine dodecylbenzene sulfonate, sodium dodecylbenzene sulfonate, calcium dodecylbenzene sulfonate, xylene sulfonic acid, dodecylbenzene sulfonic acid, an N-alkoyl sarcosinate, sodium lauroyl sarcosinate, a dialkylsulfosuccinate, an N-alkoyl sarcosine, lauroyl sarcosine, or a mixture of two or more thereof.

11. The method of claim 3 wherein the phenol-based decontaminant composition further comprises one or more sequestering agents, cosolvents, surfactants, corrosion inhibitors or buffering agents.

12. The method of claim 3 wherein the phenol-based decontaminant composition further comprises one or more soluble inorganic salts.

13. The method of claim 1 wherein the phenol-based decontaminant composition comprises o-benzyl-p-chlorophenol, o-phenylphenol, glycolic acid, dodecyl benzene sulfonic acid and hexylene glycol.

14. The method of claim 1 wherein the phenol-based decontaminant composition further comprises brine.

15. The method of claim 1 wherein the phenol-based decontaminant composition is acidic.

16. The method of claim 1 wherein the phenol-based decontaminant composition is alkaline.

17. The method of claim 1 wherein the phenol-based decontaminant composition includes water.

18. The method of claim 1 wherein prior to combining the phenol-based decontaminant composition with the protein, the phenol-based decontaminant composition is in the form of a concentrate which is diluted with water to form the solution of the phenol-based decontaminant.

19. The method of claim 1 wherein prior to combining the phenol-based decontaminant composition with the protein, the phenol-based decontaminant composition is in the form of a concentrate, the concentrate having a total phenol concentration in the range from about 0.1M to about 1.0M.

20. The method of claim 1 wherein the material which is contaminated with prions comprises a surface or a liquid body.

21. The method of claim 1 wherein the material which is contaminated with prions comprises a surface of a medical, dental or pharmaceutical instrument.

22. The method of claim 1 wherein the material which is contaminated with prions comprises the surface of equipment used in the food or beverage processing industry.

23. The method of claim 1 wherein the material which is contaminated with prions comprises a work surface, wall, floor, ceiling, fermentation tank or fluid supply line in a hospital, industrial facility or research laboratory.

24. The method of claim 1 wherein the material which is contaminated with prions comprises medical waste.

25. The method of claim 1 wherein the material which is contaminated with prions comprises blood, tissue or other body waste.

26. The method of claim 1 wherein the material which is contaminated with prions comprises a room or cage used for housing animals.

27. The method of claim 1 wherein the material which is contaminated with prions comprises a disinfection or sterilization system.

28. The method of claim 1 wherein the combining comprises combining with the protein material a solution comprising a predetermined amount of the phenol-based decontaminant; and, wherein the measuring comprises measuring the amount of phenol remaining in the solution after the combining.

* * * * *